United States Patent [19]

Vora et al.

[11] Patent Number: 5,491,275
[45] Date of Patent: Feb. 13, 1996

[54] PROCESS FOR THE DEHYDROGENATION OF PARAFFINIC HYDROCARBONS

[75] Inventors: Bipin V. Vora, Darien; Tamotsu Imai, Mount Prospect, both of Ill.

[73] Assignee: UOP, Des Plains, Ill.

[21] Appl. No.: 299,874

[22] Filed: Sep. 1, 1994

Related U.S. Application Data

[63] Continuation-in-part of Ser. No. 51,926, Apr. 26, 1993, abandoned.

[51] Int. Cl.[6] ............................. C07C 5/32; C07C 5/333
[52] U.S. Cl. .......................... 585/659; 585/324; 585/654; 585/655
[58] Field of Search ........................ 585/654, 655, 585/659, 660, 326, 330, 324

[56] References Cited

U.S. PATENT DOCUMENTS

4,430,517  2/1984  Imai et al. ..................... 585/660
4,438,288  3/1984  Imai et al. ..................... 585/379
4,761,509  8/1988  Vora et al. .................... 585/284
5,406,011  4/1995  Radcliffe et al. ............... 585/254

Primary Examiner—Ponnathapura Achutamurthy
Attorney, Agent, or Firm—Thomas K. McBride; John G. Tolomei; John G. Cutts, Jr.

[57] ABSTRACT

An improved process for the catalytic dehydrogenation of paraffinic hydrocarbons is disclosed. Feed paraffinic hydrocarbons are dehydrogenated by means of contacting the dehydrogenatable hydrocarbon with a dehydrogenation catalyst in a first dehydrogenation zone wherein the endothermic dehydrogenation reaction reduces the temperature of the resulting hydrocarbon stream containing dehydrogenated hydrocarbon compounds. The resulting effluent from the first dehydrogenation zone is then contacted with a hot hydrogen-rich gaseous stream having a temperature greater than the hydrocarbon stream to increase the temperature of the hydrocarbon stream and then introducing the resulting heated stream into a second dehydrogenation zone to produce additional dehydrogenated hydrocarbon compounds.

8 Claims, 4 Drawing Sheets

PROCESS FOR THE DEHYDROGENATION OF PARAFFINIC HYDROCARBONS

CROSS REFERENCE TO RELATED APPLICATION

This is a continuation-in-part of U.S. application Ser. No. 08/051,926 filed on Apr. 26, 1993, now abandoned.

BACKGROUND OF THE INVENTION

The field of art to which this invention pertains is the production of olefinic hydrocarbons. More specifically, the invention relates to a hydrocarbon conversion process for the selective catalytic dehydrogenation of acyclic paraffinic hydrocarbons to produce monoolefinic hydrocarbons.

INFORMATION DISCLOSURE

U.S. Pat. No. 4,761,509 (Vora et al) discloses a process for the catalytic dehydrogenation of paraffinic hydrocarbons.

U.S. Pat. No. 4,430,517 (Imai et al) discloses a new catalyst for the conversion of hydrocarbons. The catalyst comprises a platinum group component, a Group IVA component, an alkali or alkaline earth component and a porous carrier material wherein the atomic ratio of the alkali or alkaline earth component to the platinum group component is more than 10. This catalyst is particularly useful for dehydrogenating paraffins having from 2 to 5 or more carbon atoms to the corresponding mono-olefins, or for dehydrogenating mono-olefins having from 3 to 5 or more carbon atoms to the corresponding di-olefins. The patent also discloses that this catalyst may be utilized in prior art processes for the dehydrogenation of hydrocarbons, but does not disclose the preheating of a hydrogen-rich gaseous stream and subsequently mixing the heated hydrogen stream with a hydrocarbon stream prior to being fed into a subsequent reactor.

U.S. Pat. No. 4,438,288 (Imai et al) discloses a process for dehydrogenating hydrocarbons which comprises contacting a dehydrogenatable hydrocarbon in a dehydrogenation zone with a catalyst comprising a platinum group component, an alkali or alkaline earth component and a porous support material to produce a dehydrogenated hydrocarbon and a used catalyst; contacting the used catalyst in a catalyst regeneration zone with a halogen component to produce a regenerated catalyst containing added halogen component; and contacting a dehydrogenatable hydrocarbon in a dehydrogenation zone with the resulting regenerated catalyst to produce a dehydrogenated hydrocarbon and a used catalyst. The patent does not disclose the preheating of the hydrogen-rich gaseous stream and mixing the heated gaseous stream with hydrocarbon prior to being subsequently introduced into a dehydrogenation reaction zone.

The prior art utilizes large commercial reactors which are essentially adiabatic. In the case of endothermic reactions, the reaction temperature decreases as the reaction proceeds which lowers the equilibrium conversion level and, accordingly, the achievable conversion level is decreased. In order to overcome this problem, the prior art used tubular reactors so that heat can be supplied externally via heat-exchange through the tubes into the reaction zone. Tubular reactors are disadvantageous for large scale reactor systems because catalyst loading and unloading becomes an onerous and expensive operation.

Endothermic hydrocarbon conversion reactions such as dehydrogenation and dehydrocyclization are conducted while employing hydrogen co-feed in order to suppress undesirable side reactions and catalyst deactivation due to coke formation on the catalyst. The amount of hydrogen required varies along the catalyst bed because hydrogen is needed as the conversion increases.

Thus, it is not necessary to add the total amount of hydrogen at the reactor inlet and we have discovered that a minimum amount of hydrogen initially required may be added together with the hydrocarbon feed and the remaining required amount of hydrogen is heated to appropriate temperatures, divided and added into the catalyst zone at specific locations. The high temperature hydrogen supplies heat to the reactant stream in order to favorably influence the overall endothermic reaction. With the present invention, the endothermic heat of reaction is compensated by the enthalpy of the high temperature hydrogen, thereby resulting in the achievement of higher conversion.

Previously, it has been known to provide the heat of reaction in multi-stage catalytic reactions by reheating the entire effluent from one catalyst zone before it enters the next catalyst zone. This results in additional pressure drop in the system which requires a higher inlet pressure and which is disadvantageous and detrimental to the dehydrogenation equilibrium. In a typical prior art heater-reactor design, as high as 80% of the total pressure drop occurs in the heater and the inlet lines to the reactor. Furthermore, putting the entire first stage reactor effluent through a heater adds thermal residence time as well as exposes the product to high skin (wall) temperature. Dehydrogenation zone effluents are prone to thermal cracking and also have a tendency of forming coke on heat-exchange surfaces. Modern catalytic dehydrogenation processes have served the industry well, but have been handicapped by the reaction zones which are necessarily required for commercial service. Based upon a recognition of the shortcomings of the prior art, we have discovered an improved process for the dehydrogenation of hydrocarbon compounds. Therefore, it is desired that high temperature, non-catalytic residence time be minimized in accordance with the present invention.

BRIEF SUMMARY OF THE INVENTION

It has now been found that an improved dehydrogenation process can be achieved by reheating the effluent from one dehydrogenation zone with a hot hydrogen-rich gaseous stream before introducing the feed stream to a second catalytic dehydrogenation zone. In accordance with the present invention, if the improved process is operated in order to achieve a constant conversion, a higher yield of olefinic hydrocarbons is achieved while utilizing lower reactor temperatures which results in improved catalyst life and process plant operability. When the present invention is utilized and is operated at increased conversion, the same yield is expected while enjoying an increased capacity of a significant amount which results in reduced operating costs.

The invention provides a process for the dehydrogenation of a paraffinic dehydrogenatable hydrocarbon by means of contacting the dehydrogenatable hydrocarbon and hydrogen with a dehydrogenation catalyst in a first dehydrogenation zone wherein the endothermic dehydrogenation reaction reduces the temperature of the resulting hydrocarbon stream containing dehydrogenated hydrocarbon compounds. The resulting effluent from the first dehydrogenation zone is then contacted with a hot hydrogen-rich gaseous stream having a temperature greater than the hydrocarbon stream exiting from the first dehydrogenation zone to increase the temperature of the hydrocarbon stream and then introducing the resulting heated stream into a second dehydrogenation zone to produce additional dehydrogenated hydrocarbon compounds. The use of a hydrogen-rich gas heater in accordance with the present invention adds very little pressure drop to the system and the hot hydrogen-rich gas may be conveniently introduced and admixed with the flowing hydrocarbon stream close to the catalyst bed to minimize thermal degradation.

One broad embodiment of the present invention is a process for the dehydrogenation of a paraffinic dehydrogenatable hydrocarbon which process comprises: (a) contacting the paraffinic dehydrogenatable hydrocarbon and hydrogen with a dehydrogenation catalyst at dehydrogenation conditions in a first dehydrogenation zone wherein the endothermic dehydrogenation reaction reduces the temperature of a resulting hydrocarbon stream containing dehydrogenated hydrocarbon compounds; (b) contacting the hydrocarbon stream containing dehydrogenated hydrocarbon compounds produced in step (a) with a first hydrogen-rich gaseous stream having a temperature greater than the hydrocarbon stream to thereby increase the temperature of the hydrocarbon stream to dehydrogenation conditions; (c) contacting a resulting heated hydrocarbon stream produced in step (b) with a dehydrogenation catalyst at dehydrogenation conditions in a second dehydrogenation zone; (d) condensing at least a portion of an effluent from the second dehydrogenation zone to produce a liquid hydrocarbon stream comprising dehydrogenated hydrocarbon compounds and a second hydrogen-rich gaseous stream; (e) heating at least a portion of the second hydrogen-rich gaseous stream to produce the first hydrogen-rich gaseous stream of step (b); and (f) recovering dehydrogenated hydrocarbon compounds.

Other embodiments of the present invention encompass further details such as sources of hydrocarbon feed streams, dehydrogenation catalysts and dehydrogenation operating conditions, all of which are hereinafter disclosed in the following discussion of each of these facets of the invention.

DETAILED DESCRIPTION OF THE INVENTION

The production of acyclic olefinic hydrocarbons is a highly useful hydrocarbon conversion process. The product olefinic hydrocarbons find utility in the production of a wide variety of useful chemicals including synthetic lubricants, detergents, polymers, alcohols, plasticizers, etc.

The feed hydrocarbon charged to the subject process is an acyclic $C_7^+$ hydrocarbon. Preferably, the feed hydrocarbon is a normal paraffin. The upper limit on the carbon number of the charge stock is basically set by the volatility and processability of the charge stock in the dehydrogenation reactor. This upper limit is at about $C_{22}$ paraffins. The feed stream may be a high purity stream of a single paraffin or a feed stream may comprise a mixture of two or more paraffins having different carbon numbers. For instance, an admixture of $C_{10}$ to $C_{15}$ normal paraffins is often passed through a dehydrogenation zone to produce linear olefins which are consumed in the production of linear alkyl benzenes suitable for use in the production of biodegradable detergents. In accordance with the present invention, the paraffinic dehydrogenatable hydrocarbon comprises $C_{10}$ to $C_{20}$ paraffins.

Figure 1:
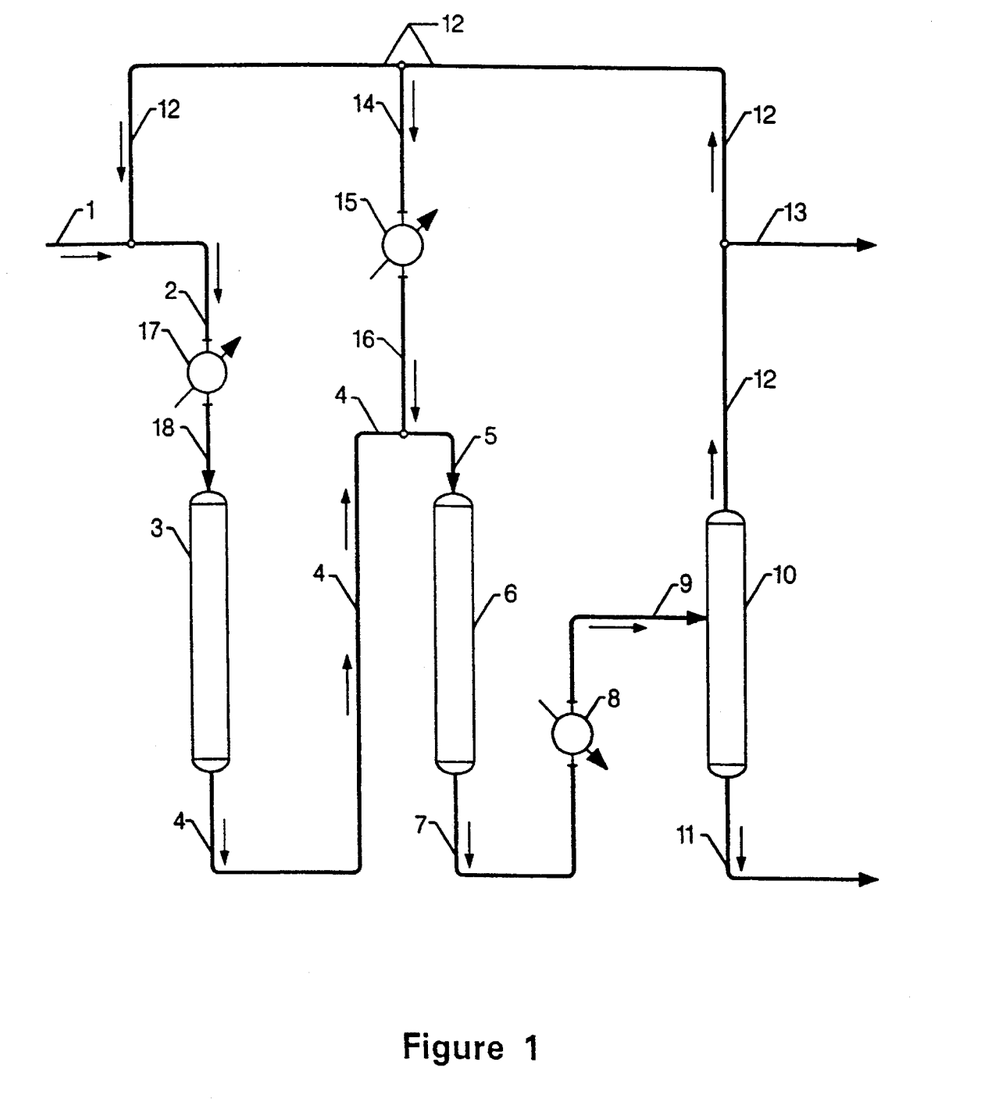
FIG. 1 is a simplified process flow diagram of a preferred embodiment of the present invention.

The equipment used in the process of the present invention is preferably configured substantially as shown in the drawing which is hereinafter described in detail, however, additional dehydrogenation zones are also contemplated. In accordance with the present invention, two or more dehydrogenation zones may be utilized, including three dehydrogenation zones, for example. In this arrangement, a fresh paraffinic hydrocarbon feed stream is combined with recycle hydrogen. This forms a reactant stream which is heated by indirect heat exchange and is then passed through a bed of a suitable catalyst maintained at the proper dehydrogenation conditions of temperature and pressure. The effluent of this catalyst bed or reactor effluent stream is then contacted with a high temperature hydrogen-rich gaseous stream which is utilized to raise the temperature of the reactant stream before introduction into a second catalyst bed. The effluent from the second catalyst bed or reactor effluent stream is cooled and partially condensed. Part of the uncondensed material is employed as the hydrogen-rich recycle gas stream. The remainder of the uncondensed hydrogen-rich material is the net production of hydrogen which may be used in other applications such as desulfurization, for example. As used herein, the term "rich" is intended to indicate a molar concentration of the indicated compound or class of compounds above 50%. In a preferred embodiment of the present invention, the hydrogen-rich gaseous stream preferably contains at least about 80 mol % hydrogen. The separation zone also produces a liquid stream referred to herein as the liquid phase process stream. This stream is basically an admixture of dehydrogenated and undehydrogenated acyclic hydrocarbons. This liquid phase stream will also contain some dissolved hydrogen and light hydrocarbons produced in various cracking reactions which occur at the high temperatures employed in the dehydrogenation reactor. In one case, this resulting liquid effluent stream is passed into a stripping column designed and operated to remove overhead all compounds which are more volatile than the lightest hydrocarbon which it is desired to have present in the net effluent stream of the dehydrogenation process. These lighter materials will be concentrated into a net overhead stream which will comprise an admixture of hydrogen and light hydrocarbons. The purpose of the stripping operation is to prevent the entrance of volatile light materials including hydrogen into downstream processing zones where they would present certain operational problems. For example, the passage of light monoolefins into an alkylation zone would lead to the production of an increased amount of undesired side products through alkylation and polymerization reactions. Other non-condensable materials under the alkylation conditions, such as hydrogen, methane and ethane, would require venting which will require scrubbing for hydrogen fluoride removal which creates waste disposal problems. The stripping column also serves to eliminate the light hydrocarbons from any recycle stream which returns paraffinic hydrocarbons to the dehydrogenation zone from a downstream processing unit. In a second case when the separation zone produces a liquid stream which contains diolefins, this liquid stream may be subjected to selective hydrogenation to convert diolefin compounds to monoolefin compounds before the liquid stream having a lower concentration of diolefins is passed into the stripping column.

The composition of the dehydrogenation catalyst is not believed to materially affect the operation of the subject process provided this catalyst meets commercial standards for activity, stability, and selectivity. Dehydrogenation catalysts are described in U.S. Pat. Nos. 3,274,287; 3,315,007; 3,315,008; 3,745,112; and 4,430,517. These catalysts comprise a platinum group component supported on a porous carrier material. The preferred carrier material is a refractory inorganic oxide such as gamma-alumina. The preferred dehydrogenation catalysts contain on an elemental basis 0.01 to 2 wt. % platinum group component and about 0.1 to 5 wt. % of an alkali or alkaline earth metal. Preferably, there is present 0.05 to 1 wt. % platinum group component and about 0.25 to 3.5 wt. % of the alkali or alkaline earth component. The platinum group component may be chosen from the group consisting of platinum, palladium, rhodium, ruthenium, osmium and iridium, but platinum is highly preferred. The alkali or alkaline earth component may be selected from the group consisting of the alkali metals-cesium, rubidium, potassium, sodium, and lithium; and the alkaline earth metals-calcium, strontium, barium, and magnesium. This component is preferably either lithium or potassium. Another example of a suitable dehydrogenation catalyst is a catalyst which, in addition to the previously described platinum and alkali or alkaline earth metal components, contains a tin component. This catalytic composite would contain from 0.1 to about 1 wt. % tin. Yet another catalytic composite which should be highly suited for use in the subject process comprises an indium component in addition to the platinum, tin and alkali or alkaline earth components. The indium component may be present on an elemental basis equal to about 0.1 to about 1 wt. % of the final composite. It is also known in the art that some catalytic composites of this nature may benefit from the presence of a small amount of a halogen component, with chlorine being the normally preferred halogen. Typical halogen concentrations in the final catalytic composite range from about 0.1 to about 1.5 wt. %. A halogen component is not desired in all situations. These catalytic composites are known to those skilled in the art and are described in the available references.

In accordance with the present invention, dehydrogenation conditions include a pressure from about 0 psig to about 50 psig (345 kPa gauge) and a temperature from about 752° F. (400° C.) to about 1022° F. (550° C). The temperature of the hydrogen-rich gaseous stream which is utilized to heat the hydrocarbon feed to reaction temperature is preferably from about 932° F. (500° C.) to about 1292° F. (700° C).

The net product of the process, the bottoms stream of the stripping column, can be passed into a number of downstream processing units or it can be withdrawn as a finished product. For instance, the product stream may be passed into alkylation zones wherein the olefinic hydrocarbons can be reacted with aromatic hydrocarbons or into esterification zones as in the production of plasticizers. The product stream may also be passed into an oligomerization zone or a hydration zone. Another possibility is that the net process effluent stream may be charged to a separation zone which separates the monoolefins from the unconverted paraffins. This separation could be performed by fractional distillation on a single carbon number effluent stream but would be quite a difficult and expensive fractionation. Sorptive-type separations which employ selective solid adsorbents, known in the art, are preferred for this type of separation. A broad carbon number range olefin-paraffin mixture can be charged to such a process and efficiently separated into a high purity olefin stream and a paraffin stream. The paraffin stream may then be recycled to the dehydrogenation zone.

The process of the present invention enjoys the unexpected advantages presented hereinabove because in a dehydrogenation process that is operated at a temperature of about 932° F. (500° C.), a typical normal paraffin feed stream undergoes a thermal cracking loss of about 0.5 weight percent during a one second residence time at this temperature (932° F). In addition, if this typical normal paraffin feed stream is passed through a first catalytic dehydrogenation zone and contains about 16 percent olefinic hydrocarbons, is subjected to the same temperature of 932° F. (500° C.), there is a thermal cracking loss of more than 1 weight percent during a one-second residence time at this temperature.

In order to minimize the undesirable thermal conversion associated with these high temperatures, the dehydrogenation reaction zones are commercially operated at lower temperatures where the equilibrium conversion is only about 16 percent per pass which means that, in order to achieve complete conversion of an n-paraffin feed stream, the paraffins must be subjected to up to six passes. At a reasonable temperature below 932° F. (500° C.), the thermal cracking loss between a pure normal paraffin feed stream and a normal paraffinic feed stream containing about 16 percent olefinic hydrocarbon is about 0.6 weight percent. Therefore, if six passes are required for complete conversion, the total thermal loss is 3.6 weight percent (6×0.6–3.6). Then, if a stream containing olefinic hydrocarbons can be heated without passing through a heater at significant residence times, the undesirable thermal conversion of useful and valuable hydrocarbons may be minimized by the use of the present invention. This savings may represent the difference between an economically viable process and one that is not.

In FIG. 1, one embodiment of the present invention is illustrated by means of a simplified flow diagram in which such details as pumps, instrumentation, heat exchange and heat-recovery circuits, compressors and similar hardware have been deleted as being non-essential to the understanding of the techniques involved. The use of such miscellaneous equipment is well within the purview of one skilled in the art of petroleum refining and petrochemical production techniques.

Referring now to FIG. 1, a paraffin feed stream comprising an admixture of $C_{10}$–$C_{15}$ normal paraffins enters the process through line 1. This feed stream is admixed with hydrogen from line 12 and is passed by line 2 into heater 17 to achieve reaction temperature. The resulting heated feed stream is removed from heater 17 and is introduced via line 18 into reaction zone 3 which is operated at dehydrogenation conditions. The effluent from reaction zone 3 is transported via line 4 and is admixed with a heated hydrogen-rich gaseous stream provided via line 16 to form a heated reactant stream which is introduced via line 5 into reaction zone 6. The resulting effluent containing dehydrogenated hydrocarbons is removed from reaction zone 6 via conduit 7 and introduced into heat exchanger 8. Heat exchanger 8 is used to cool the flowing stream and line 9 is used to transport the resulting cooled stream into vapor-liquid separator 10. A resulting liquid stream containing dehydrogenated hydrocarbon compounds is removed from vapor-liquid separator 10 via conduit 11 and recovered. A hydrogen-rich gaseous stream ($H_2$–91.5 mol %; $C_1$–2 mol %; $C_2$–4 mol %; $C_3$–1.5 mol %; $C_4$–1.0 mol %; Total olefins= 0.25 mol %) is removed from vapor-liquid separator 10 via conduit 12 and a net hydrogen gas stream is removed from the process via conduit 13. Another portion of the hydrogen-rich gaseous stream resulting from vapor-liquid separator 10 is transported via line 12 and line 14 and is introduced into heat exchanger 15 wherein the temperature of the flowing stream is increased. The resulting heated hydrogen-rich gaseous stream is removed from heat exchanger 15 and transported via line 16 as hereinabove described. Another portion of the hydrogen-rich gaseous stream which is removed from vapor-liquid separator 10 is transported via line 12 and is admixed with the incoming fresh hydrocarbon feed as hereinabove described.

The following illustrative embodiments are presented for the purpose of further illustrating the process of the present invention and to demonstrate the advantages realized from the use of the process. The following data were not completely obtained by the actual performance of the present invention, but are considered prospective and reasonably illustrative of the expected performance of the invention.

ILLUSTRATIVE EMBODIMENT 1

A paraffin feed stream comprising an admixture of $C_{10}$–$C_{15}$ normal paraffins ($C_{10}$–10 wt. %; $C_{11}$–18 wt. %; $C_{12}$–22 wt. %; $C_{13}$–34 wt. %; $C_{14}$–14 wt. %; $C_{15}$–2 wt. %) is introduced with essentially pure hydrogen containing no olefinic hydrocarbons into a dehydrogenation zone containing a dehydrogenation catalyst comprising alumina and platinum and maintained at dehydrogenation conditions including a molar hydrogen to normal paraffin ratio of 6:1, a reactor inlet temperature of 882° F. (472° C.) and a pressure of 20 psig. The reactor effluent contained 12 mol percent monoolefin. This is identified as Run A.

Another paraffin feed stream having the same characteristics as the feed stream in Run A is converted in a dehydrogenation zone containing a dehydrogenation catalyst comprising alumina and platinum with one-half of the catalyst located in a first reactor and one-half of the catalyst located in a second reactor. The total volume of catalyst was the same as in Run A. The feed stream is introduced into the first reactor in admixture with about 60% of the total hydrogen used in Run A at a reactor inlet temperature of 472° C. and a pressure of 20 psig. The effluent from Reactor 1 which contains 10 mol % monoolefin is admixed with 40% of the total hydrogen used in Run A having a temperature of 1100° F. (593° C.) to produce a feed having a temperature of 882° F. (472° C.) which is introduced into the second reactor. The hydrogen used in both Run A and Run B is 99% pure and contains no olefinic hydrocarbons. The effluent from the second reactor contained 15 mol percent monoolefin. This is identified as Run B. The results of Run A and Run B are summarized and presented in Table 1.

TABLE 1

SUMMARY OF RESULTS

| | Run A | Run B |
|---|---|---|
| Reactor 1, Catalyst Volume, % | 100 | 50 |
| Reactor 2, Catalyst Volume, % | — | 50 |
| Hydrogen to Reactor 1, % | 100 | 60 |

TABLE 1-continued

SUMMARY OF RESULTS

| | Run A | Run B |
|---|---|---|
| Hydrogen to Reactor 2, % | — | 40 |
| Reactor 1, Inlet Temperature, °C. | 472 | 472 |
| Reactor 2, Inlet Temperature, °C. | — | 472 |
| Monoolefins, mol % | 12 | 15 |

ILLUSTRATIVE EMBODIMENT 2

The following study was conducted to determine the cracking losses for four cases.

Case 1 is a single reactor (one stage) prior art dehydrogenation process using a paraffin feed stream comprising an admixture of $C_{10}$–$C_{15}$ normal paraffins which process is operated at a reactor inlet temperature of 472° C. and resulting in a product containing 12 mol percent monoolefins. With a thermal residence time of 1.25 seconds in the charge heater, transfer line and reactor inlet piping, 0.20 weight percent of the hydrocarbon fresh feed is thermally cracked. Another 0.20 weight percent of the hydrocarbon fresh feed is catalytically cracked into side-reaction products resulting in a total cracking loss of 0.40 weight percent of the hydrocarbon fresh feed or 3.0 weight percent of the fresh feed that is converted. These results are summarized in Table 2.

Case 2 is similar to Case 1 with the exception that the reactor inlet temperature is increased to 490° C. to obtain in a one-stage process the same product monoolefin content (15%) as for the two-stage cases presented hereinafter. In Case 2, the higher temperature results in an increase in thermal and catalytic cracking. Cracking losses are 0.50 weight percent thermal and 0.42 weight percent catalytic for a total loss of 0.92 weight percent of the reactor feed or 5.5 weight percent of the feed that is converted. These results are summarized in Table 2.

Case 3 is a two-stage dehydrogenation process with 50% of the catalyst in the first stage or reactor and 50% of the catalyst in the second stage or reactor and an interheater to reheat the product of stage 1 to 472° C. which is the inlet temperature for both stages. For this case a one second thermal residence time is used for both the feed to stage 1 and the stage 1 product to stage 2. The total thermal cracking loss is 0.65 weight percent of the reactor feed (0.16 weight percent at the inlet of stage 1 and 0.49 weight percent at the inlet to stage 2). This case has an 0.39 weight percent catalytic cracking loss and the total cracking loss is 1.04 weight percent of the reactor feed or 6.1% of the feed that is converted. These results are resummarized in Table 2.

Case 4 is a two-stage dehydrogenation process whereby 60% of the hydrogen recycle gas is sent to stage 1 and the remaining 40% of hydrogen recycle gas is heated to 593° C. (1100° F.) to provide the interheat when combined with the product of stage 1. Case 4 exemplifies the process of the present invention. The use of hot hydrogen instead of an interheater reduces the pressure in stage 1 by 2 psi and reduces the hot residence time at stage 2 inlet from 1.0 to 0.5 seconds. The total thermal cracking loss is 0.40 weight percent of the reactor feed (0.16 weight percent at the inlet of stage 1 and 0.24 weight percent at the inlet of stage 2). This case has an 0.36 weight percent catalytic cracking loss and the total cracking loss is 0.76 weight percent of the reactor feed or 4.6 weight percent of the feed that is converted. These results are also summarized and presented in Table 2.

From Table 2, it can be seen that in a one-stage operation when the conversion severity is increased from 12 to 15 weight percent monoolefins (as in Case 1 to Case 2), the total cracking loss as a percent of feed converted increased from 3.0 to 5.5. In Case 3, a two-stage dehydrogenation process with an interheater produces an effluent product with 15 weight percent monoolefins, but the total cracking loss as a percent of feed converted was 6.1. Case 4 exemplifies the process of the present invention and produces an effluent product with 15 weight percent monoolefins, but the total cracking loss as a percent of feed converted was only 4.6 weight percent.

TABLE 2

SUMMARY OF RESULTS

|  | Case 1 1 Stage | Case 2 1 Stage Increased Conversion | Case 3 2 Stage w/Inter-heater | Case 4 2 Stage w/Split $H_2$ |
|---|---|---|---|---|
| Reactor 1, Catalyst Volume, % | 100 | 100 | 50 | 50 |
| Reactor 2, Catalyst Volume, % | — | — | 50 | 50 |
| $H_2$ to Reactor 1, % | 100 | 100 | 100 | 60 |
| $H_2$ to Reactor 2, % | — | — | — | 40 |
| Reactor 1 Inlet Temp., °C. | 472 | 490 | 472 | 472 |
| Reactor 2, Inlet Temp., °C. | — | — | 472 | 472 |
| Monoolefins, Wt. % | 12 | 15 | 15 | 15 |
| Cracking Loss, % Feed Converted |  |  |  |  |
| Thermal | 1.5 | 3.0 | 3.8 | 2.4 |
| Catalytic | 1.5 | 2.5 | 2.3 | 2.2 |
| Total | 3.0 | 5.5 | 6.1 | 4.6 |

EXAMPLE 1

A paraffin feed stream comprising an admixture of $C_{10}$–$C_{15}$ normal paraffins was introduced into a thermal zone for a one-second residence time at various temperatures ranging from 400° C. to 510° C. and the amount of thermal cracking of the paraffins was determined. These results were used to plot line A in FIG. 2.

A paraffin/olefin feed stream comprising an admixture of $C_{10}$–$C_{15}$ normal hydrocarbon compounds and containing 13 mol percent monoolefins was introduced into a thermal zone for a one-second residence time at various temperatures ranging from 400° C. to 510° C. and the amount of thermal cracking of the paraffin/olefin feed was determined. These results were used to plot line B in FIG. 2.

Figure 2:
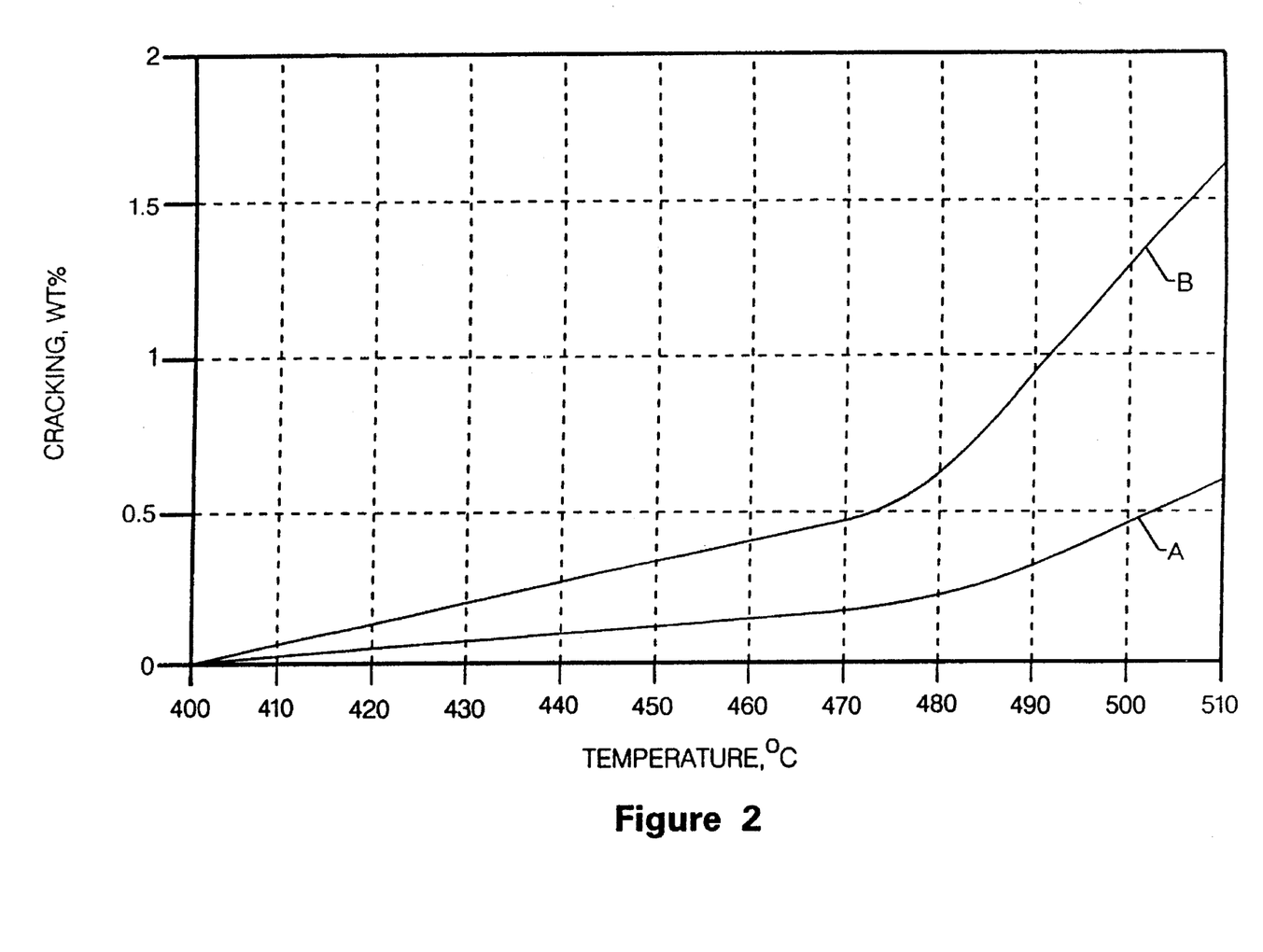
FIG. 2 shows the amount of thermal cracking of a normal paraffin feed stream and a normal paraffin/olefin feed stream as a function of temperature.

FIG. 2, line A, demonstrates the rate of thermal cracking of a $C_{10}$–$C_{15}$ normal paraffin stream as a function of increasing temperature. Line B of FIG. 2 demonstrates the rate of thermal cracking of a paraffin/olefin stream comprising an admixture of $C_{10}$–$C_{15}$ normal hydrocarbon compounds and containing 13 mol percent monoolefins. It can be readily seen that the thermal cracking rate for the hydrocarbon stream containing olefins is greater than that of a pure paraffin hydrocarbon stream and that the rate rapidly accelerates at a temperature greater than 470° C. Therefore, the advantages of not subjecting a stream containing olefinic hydrocarbons to heating in a heater is readily apparent.

EXAMPLE 2

A paraffin feed stream comprising an admixture of $C_{10}$–$C_{15}$ normal paraffins was introduced into a two-stage reaction zone with split hydrogen flow in accordance with the present invention. Each of the two catalyst zones contained 50% of the total catalyst and 60% of the hydrogen recycle was sent to stage 1 and the remaining hydrogen recycle gas is heated to provide the interheat when combined with the product of stage 1. The inlet to each catalyst zone is maintained at 468° C. The overall hydrogen to hydrocarbon mole ratio was 6 and the pressure was maintained at 20 psig. The conversion of normal paraffins in the fresh feed was 16%. The results from Example 2 are plotted in FIG. 3 as line B and line C. The reaction equilibrium curve is represented by line A. The product effluent from the second catalyst zone (stage 2) contained 14 mol percent monoolefin hydrocarbon.

Figure 3:
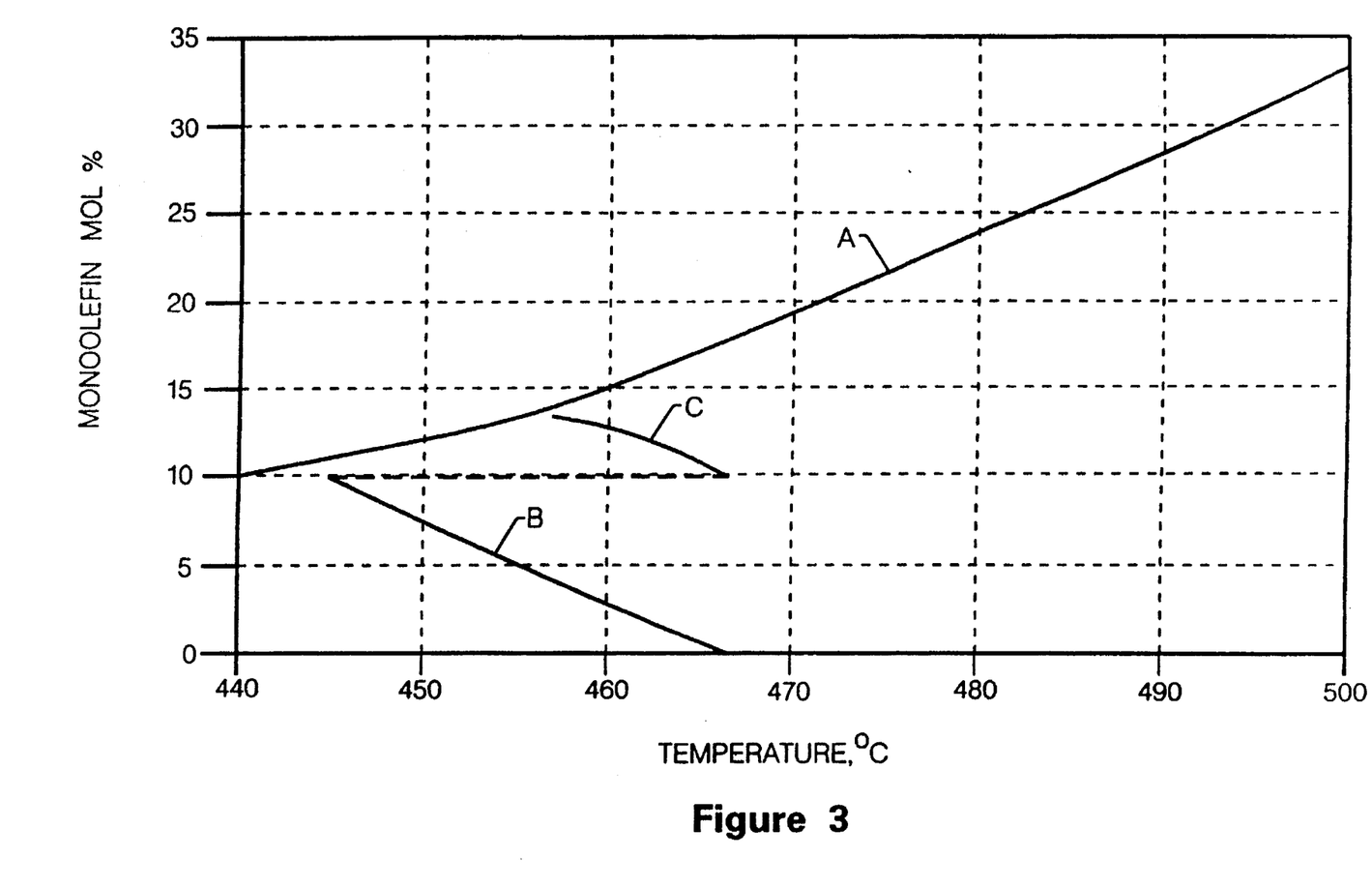
FIG. 3 shows the amount of monoolefin hydrocarbon produced from a $C_{10}$–$C_{15}$ normal paraffin feed stream in a two-stage reaction zone with split hydrogen flow in accordance with the present invention as a function of temperature.

Line B represents the temperature decrease from 468° C. of the fresh feed during the conversion in stage 1 as a function of the increasing monoolefin content to 10 mol percent. The effluent from stage 1 had a temperature of 445° C. and the effluent was heated with hot hydrogen recycle to 468° C. and introduced into stage 2 or the second catalyst zone. Line C represents the temperature decrease from 468° C. during the conversion in stage 2 as a function of the increasing monoolefin content to 14 mol percent monoolefin hydrocarbon.

EXAMPLE 3

A paraffin feed stream comprising an admixture of $C_{10}$–$C_{15}$ normal paraffins was introduced into a single stage reaction zone. The catalyst zone contained the total amount of catalyst used in Example 2. The operating conditions included a hydrogen to hydrocarbon mol ratio of 6 and a pressure at 20 psig. In order to produce a product effluent from the single stage reaction zone containing 14 mol percent monoolefin hydrocarbon, the catalyst inlet temperature had to be raised to 492° C. in contrast with the temperature of 468° C. required in Example 2. The conversion of normal paraffins in the fresh feed was 16%. The results from Example 3 are plotted in FIG. 4 as line B. The reaction equilibrium curve is represented by line A.

Figure 4:
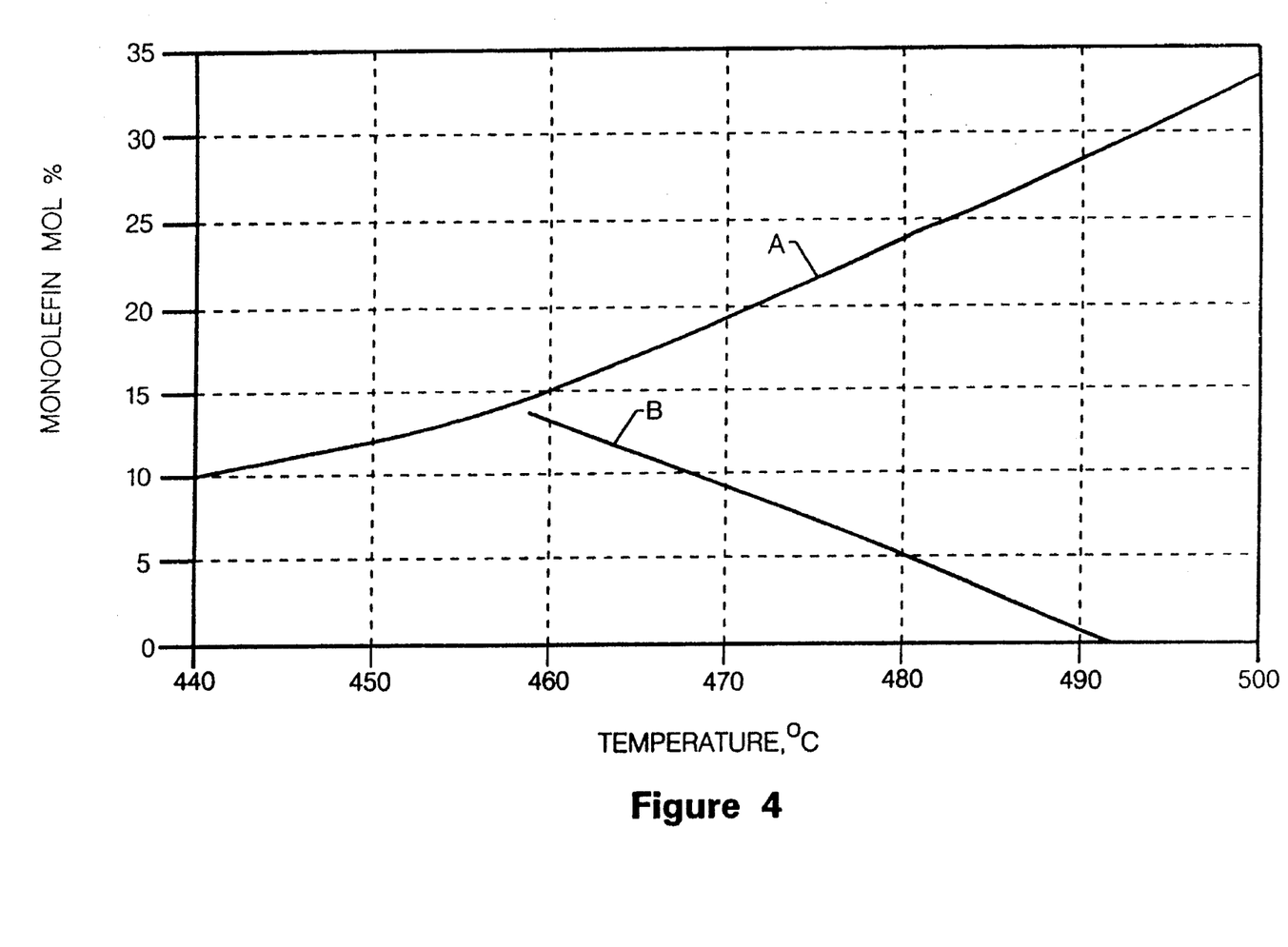
FIG. 4 shows the amount of monoolefin hydrocarbon produced from a $C_{10}$–$C_{15}$ normal paraffin feed stream in a single stage reaction zone as a function of temperature.

Line B represents the temperature decrease from 492° C. of the fresh feed during the conversion in the single catalyst zone as a function of the increasing monoolefin content to 14 mol percent. Since it has been shown hereinabove the advantages of performing the desired dehydrogenation conversion at the lowest possible temperature in order to avoid undesirable thermal conversion, the advantages enjoyed by the present invention are readily apparent.

The foregoing description, drawings, illustrative embodiments and examples clearly illustrate the advantages encompassed by the process of the present invention and the benefits to be afforded with the use thereof.

What is claimed is:

1. A process for the dehydrogenation of a paraffinic dehydrogenatable hydrocarbon which process comprises:
   (a) contacting said paraffinic dehydrogenatable hydrocarbon and hydrogen with a dehydrogenation catalyst at dehydrogenation conditions in a first dehydrogenation zone wherein the endothermic dehydrogenation reaction reduces the temperature of a resulting hydrocarbon stream containing dehydrogenated hydrocarbon compounds;
   (b) contacting said hydrocarbon stream containing dehydrogenated hydrocarbon compounds produced in step (a) with a first hydrogen-rich gaseous stream having a temperature greater than said hydrocarbon stream to thereby increase the temperature of said hydrocarbon stream to dehydrogenation conditions;

(c) contacting a resulting heated hydrocarbon stream produced in step (b) with a dehydrogenation catalyst at dehydrogenation conditions in a second dehydrogenation zone;

(d) condensing at least a portion of an effluent from said second dehydrogenation zone to produce a liquid hydrocarbon stream comprising dehydrogenated hydrocarbon compounds and a second hydrogen-rich gaseous stream;

(e) heating at least a portion of said second hydrogen-rich gaseous stream to produce said first hydrogen-rich gaseous stream of step (b); and (f) recovering dehydrogenated hydrocarbon compounds.

2. The process of claim 1 wherein said paraffinic dehydrogenatable hydrocarbon comprises $C_{10}$ to $C_{15}$ paraffins.

3. The process of claim 1 wherein said paraffinic dehydrogenatable hydrocarbon comprises $C_{15}$ to $C_{20}$ paraffins.

4. The process of claim 1 wherein said dehydrogenation conditions include a pressure from about 0 psig to about 50 psig (345 kPa gauge) and a temperature from about 752° F. (400° C.) to about 1022° F. (550° C.).

5. The process of claim 1 wherein the temperature of said first hydrogen-rich gaseous stream is in the range from about 932° F. (500° C.) to about 1292° F. (700° C.).

6. The process of claim 1 wherein said liquid hydrocarbon stream produced in step (d) contains diolefin hydrocarbon compounds.

7. The process of claim 1 wherein said first hydrogen-rich gaseous stream comprises at least about 80 mol % hydrogen.

8. The process of claim 1 wherein said second hydrogen-rich gaseous stream comprises at least about 80 mol % hydrogen.

* * * * *